US008424737B2

(12) United States Patent
Scirica

(10) Patent No.: US 8,424,737 B2
(45) Date of Patent: Apr. 23, 2013

(54) ROTATING KNOB LOCKING MECHANISM FOR SURGICAL STAPLING DEVICE

(75) Inventor: Paul A. Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 99 days.

(21) Appl. No.: 12/478,364

(22) Filed: Jun. 4, 2009

(65) Prior Publication Data

US 2009/0236395 A1 Sep. 24, 2009

Related U.S. Application Data

(63) Continuation of application No. 11/520,343, filed on Sep. 11, 2006.

(51) Int. Cl.
*A61B 17/068* (2006.01)
(52) U.S. Cl.
USPC .................. 227/175.2; 227/175.1; 227/179.1
(58) Field of Classification Search ............... 227/175.1, 227/175.2, 175.3, 179.1
See application file for complete search history.

(56) References Cited

U.S. PATENT DOCUMENTS

| | | | | |
|---|---|---|---|---|
| 4,728,020 A | * | 3/1988 | Green et al. ................... 227/19 |
| 5,071,052 A | * | 12/1991 | Rodak et al. ............... 227/175.2 |
| 5,137,198 A | | 8/1992 | Nobis et al. |
| 5,465,894 A | | 11/1995 | Clark et al. |
| 5,762,255 A | | 6/1998 | Chrisman et al. |
| 5,762,256 A | * | 6/1998 | Mastri et al. ............... 227/176.1 |
| 5,772,099 A | | 6/1998 | Gravener |
| 5,782,397 A | | 7/1998 | Koukline |
| 5,820,009 A | | 10/1998 | Melling et al. |
| 5,951,552 A | | 9/1999 | Long et al. |
| 6,010,054 A | | 1/2000 | Johnson et al. |
| 6,109,500 A | | 8/2000 | Alli et al. |
| 6,656,193 B2 | | 12/2003 | Grant et al. |
| 6,978,921 B2 | | 12/2005 | Shelton, IV et al. |
| 6,981,628 B2 | * | 1/2006 | Wales ........................ 227/178.1 |
| 6,988,649 B2 | * | 1/2006 | Shelton et al. ............. 227/175.2 |
| 7,500,979 B2 | | 3/2009 | Hueil et al. |
| 7,694,865 B2 | * | 4/2010 | Scirica ....................... 227/175.2 |
| 2002/0117534 A1 | | 8/2002 | Green et al. |

(Continued)

FOREIGN PATENT DOCUMENTS

| | | |
|---|---|---|
| DE | 10132358 | 1/2003 |
| EP | 0702937 | 3/1996 |
| EP | 0736285 | 10/1996 |
| WO | WO 02/43582 | 6/2002 |

OTHER PUBLICATIONS

European Search Report for EP 07017289.5-1526 date of completion is Dec. 13, 2007 (10 pages).

*Primary Examiner* — Hemant M Desai
*Assistant Examiner* — Gloria R Weeks

(57) ABSTRACT

A surgical stapling device having a rotating knob locking mechanism, and a method of using the surgical stapling device is disclosed. The surgical stapling device includes a housing, an actuation member, an elongated body portion rotatably supported on the housing, and a locking mechanism for preventing the rotation of the elongate body portion, the locking mechanism being automatically engaged upon actuation of the actuation member. The stapling device further includes a knob for rotating the elongated body portion. The locking mechanism includes a pivotably mounted member configured to engage the knob. The stapling device may further include an articulating tool assembly and an articulation lever for articulating the tool assembly. The articulation lever may be disposed on the knob for rotating the elongated body portion.

13 Claims, 8 Drawing Sheets

U.S. PATENT DOCUMENTS

| | | |
|---|---|---|
| 2004/0232201 A1 | 11/2004 | Wenchell et al. |
| 2005/0067459 A1 | 3/2005 | Swayze et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0184125 A1 | 8/2005 | Marczyk |
| 2006/0043147 A1 | 3/2006 | Mastri et al. |

\* cited by examiner

ROTATING KNOB LOCKING MECHANISM FOR SURGICAL STAPLING DEVICE

CROSS-REFERENCE TO RELATED APPLICATIONS

This application is a continuation of U.S. application Ser. No. 11/520,343 filed Sep. 11, 2006, and the disclosures of each of the above-identified applications are hereby incorporated by reference in their entirety.

BACKGROUND

1. Technical Field

The present disclosure relates to a surgical stapling device having a rotatable stapling head for applying staples to tissue. More particularly, the disclosure relates to a surgical stapling device having a locking mechanism for preventing the rotation of the stapling head.

2. Background of Related Art

Surgical devices for grasping or clamping tissue between opposed jaw structures of a tool assembly and thereafter fastening the clamped tissue are known in the art. U.S. Patent Application No. 2004/0232201, the disclosure of which is incorporated by reference in its entirety, discloses such a surgical stapling device.

Laparoscopic and/or endoscopic surgical procedures are performed through a small incision or through a narrow cannula inserted through a small entrance wound in a patient. In conventional or open procedures, surgeons directly access an operative site. Because of reduced patient trauma, shortened patient recovery periods and substantial reduction in overall cost, laparoscopic procedures are preferred over open procedures. In order to address the specific needs of endoscopic and/or laparoscopic surgical procedures, endoscopic surgical stapling devices have been developed which provide a surgeon with greater manipulability of the stapling head of the surgical device.

The stapling head of a surgical device for use in endoscopic and/or laparoscopic procedures is mounted on the distal end of an elongate shaft, permitting the stapling head to be inserted through the small incision or narrow cannula. The proximal end of the elongated shaft is rotatably supported by the stapler handle. The ability to rotate the elongate shaft allows the surgeon to selectively orient the stapling head to better grasp or engage tissue. Typically, these stapling devices include a knob positioned about the proximal end of the elongate shaft to provide a gripping means for rotatably orienting the stapling head. Tyco Healthcare Group, LP has manufactured and marketed endoscopic stapling instruments including a rotating knob, such as the MULTIFIRE ENDO GIA *30, MULTIFIRE ENDO GIA *60 and ENDO GIA *Universal for several years. These instruments have provided significant clinical benefits to the field of endoscopic surgery.

It would be beneficial to have a surgical stapling device that includes a locking mechanism for preventing the rotation of the stapling head once the surgeon has oriented the stapling head in the desired location.

SUMMARY

According to an aspect of the present disclosure, a surgical stapling device having a rotating knob locking mechanism is provided. The surgical stapling device includes a housing, an actuation member, an elongated body portion rotatably supported on the housing, and a locking mechanism for preventing the rotation of the elongate body portion, the locking mechanism being automatically engaged upon actuation of the actuation member. The locking mechanism of the surgical stapling device includes a pivotably mounted member configured to engage the knob.

The surgical stapling device further includes a knob for rotating the elongated body portion and may include an articulating tool assembly. An articulation member may be included for articulating the tool assembly. The articulation member is disposed on the knob that is used to rotate the elongated body portion.

The surgical stapling device further includes a handle assembly. The handle assembly includes a handle operably connected to the actuation member. The triggering of the handle engages the locking mechanism. Conversely, release of the handle disengages the locking mechanism. The locking mechanism of the surgical stapler is automatically disengaged upon release of the actuation member.

In another embodiment, a surgical stapling device includes a handle assembly including an actuation member, an elongated body member rotatably supported on the handle assembly, and a locking means for preventing the rotation of the elongated body member upon actuation of said actuation member. The surgical stapling device includes a knob for rotating the elongated body portion and an articuable tool assembly on the distal end of the elongated body portion.

In another embodiment, the handle assembly further includes a handle operably connected to the actuation member. The movement of the trigger engages the locking mechanism. The locking mechanism includes a pivotably mounted member configured to engage the knob. The pivotably mounted member may comprise any shape including a flat pad, cylinder or square, and may also include an o-ring or a rough surface for frictionally engaging the knob.

BRIEF DESCRIPTION OF THE DRAWINGS

The foregoing objects and advantages of the present invention may be more readily understood by one skilled in the art with reference being had to the following detailed description of preferred embodiments thereof, taken in conjunction with the accompanying drawings in which.

DETAILED DESCRIPTION OF PREFERRED EMBODIMENTS

Figure 1:
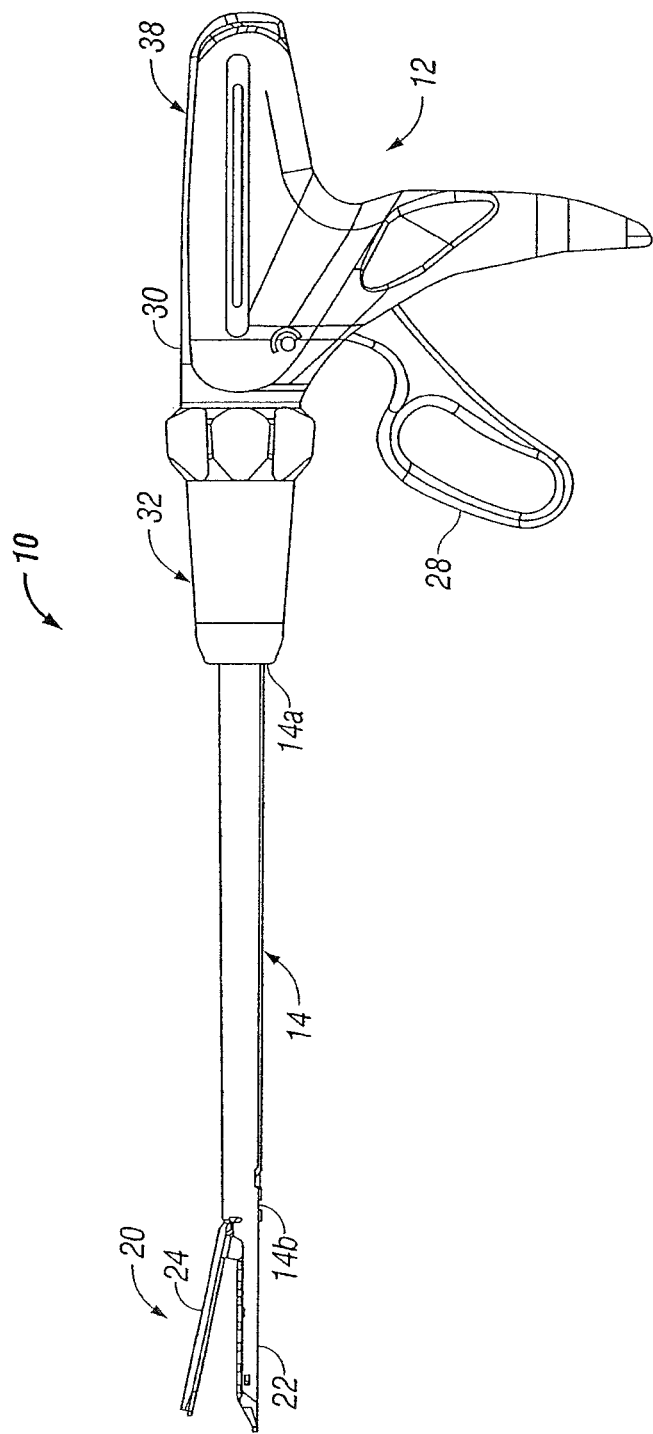
FIG. 1 is a side view of a surgical stapling device having a rotating knob locking mechanism in accordance with the present disclosure.

Preferred embodiments of the presently disclosed surgical stapling device will now be described in detail with reference to the drawings in which like reference numerals designate identical or corresponding elements in each of the several views. In the description that follows, the term "proximal", as is traditional, will refer to the end of the stapling device which is closest to the operator, while the term "distal" will refer to the end of the device which is furthest from the operator.

FIGS. 1-5 illustrate one preferred embodiment of the presently disclosed surgical stapling device shown generally as 10. It is appreciated that surgical stapling devices are well known in the art and may include any number of various features depending on the application. As such, surgical stapling device 10 will only be described in detail as relates to the locking mechanism of the present disclosure.

Figure 2:
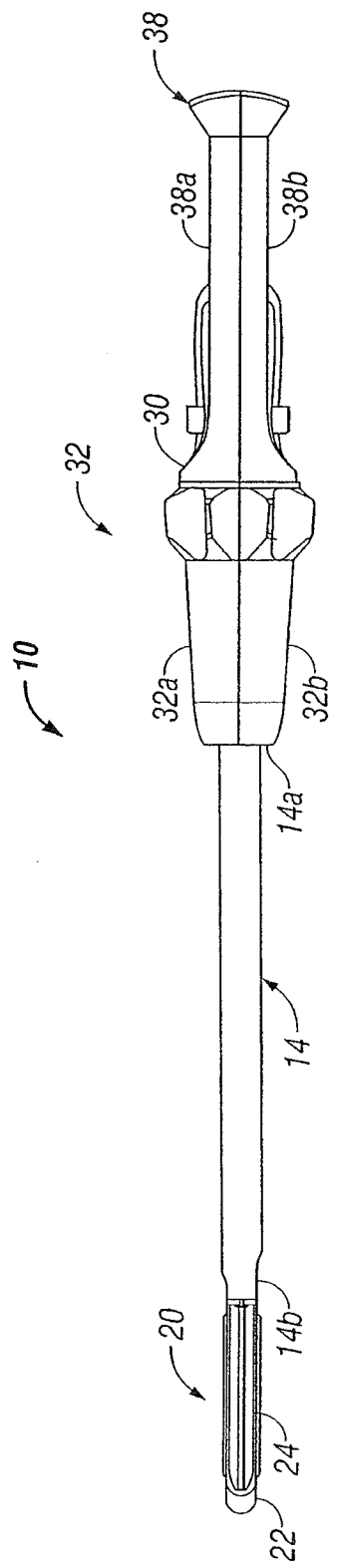
FIG. 2 is a top view of the surgical stapling device of FIG. 1.

Referring now to FIGS. 1 and 2, surgical stapling device 10 includes a handle assembly 12 and an elongated body 14. Handle assembly 12 includes a stationary handle member 26, a movable handle or trigger 28 and a barrel portion 30. Handle assembly 12 further includes housing 38 and is preferably formed from plastic molded housing half-sections 38a and 38b. Alternately, other materials may be used to form the housing including metals, e.g., stainless steel. Housing 38 forms stationary handle 26 and barrel portion 30 of handle assembly 12. Movable handle 28 is rotatably supported between housing half-sections 38a and 38b. A rotatable member or knob 32 is rotatably mounted to the forward end of barrel portion 30 and secured to the proximal end 14b of elongated body member 14. Rotatable member 32 is configured to facilitate rotation of elongated body member 14 in relation to handle assembly 12. Rotatable member 32 is preferably formed from plastic molded member half-sections 32a and 32b. Rotatable member 32 may further be grooved or knurled to facilitate gripping. A tool assembly 20 is supported on distal end 16a of elongated body 16. Tool assembly 20 includes a cartridge assembly 22 and an anvil assembly 24.

Figure 3:
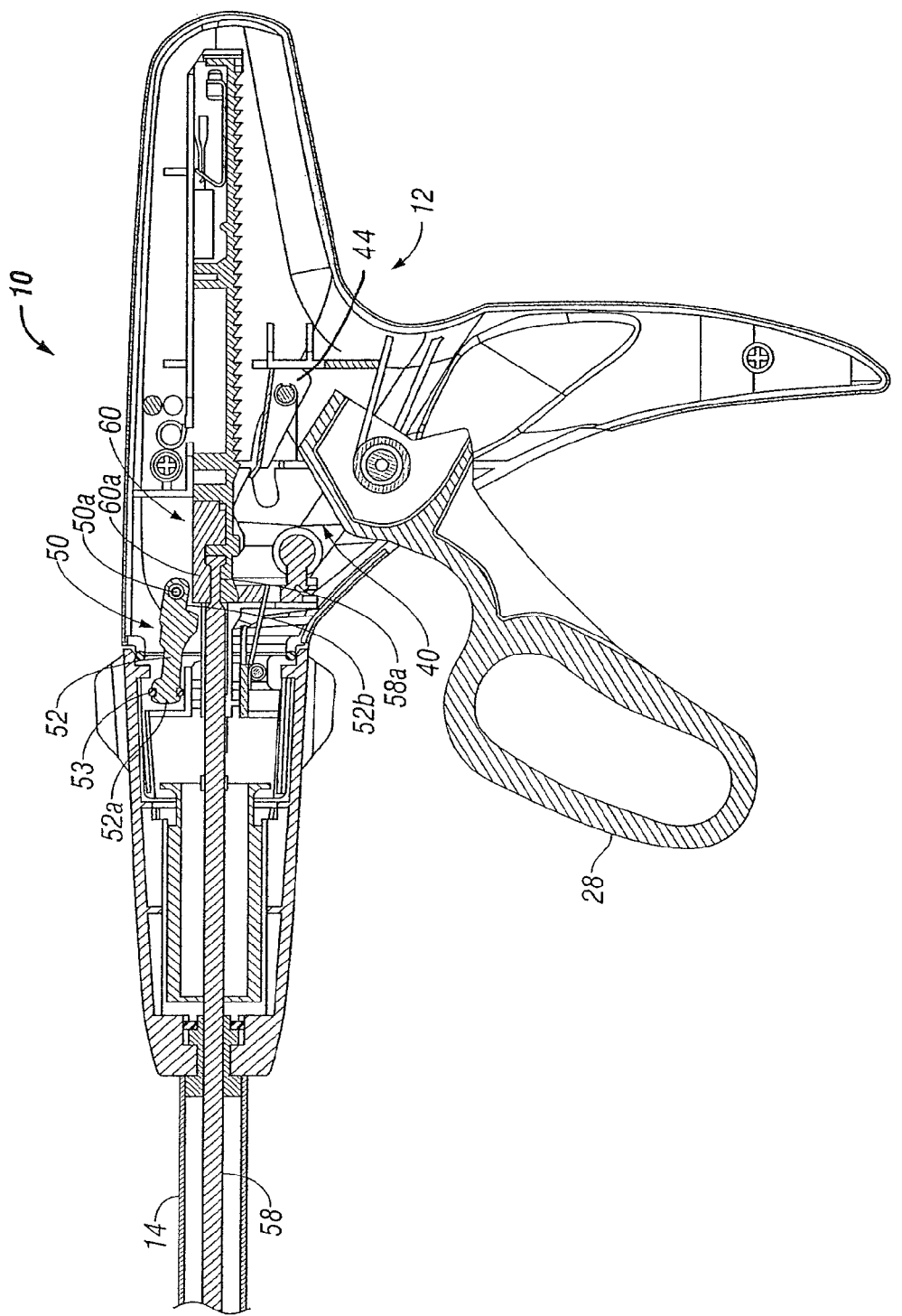
FIG. 3 is a partial cross-sectional side view of the surgical stapling device of FIGS. 1-2.

Referring now to FIG. 3, handle assembly 12 further includes an actuation mechanism 40 operably connected to movable handle 28. Actuation mechanism 40 includes a spring loaded pawl 44 configured to engage and advance a toothed rack 60 when movable handle 28 is operated. Toothed rack 60 is operably connected to the proximal end 58a of a firing rod 58. Firing rod 58 extends the length of elongated body 14. The distal end of firing rod 58 is configured to operably connect with tool assembly 20 (FIG. 2). In alternate embodiments, firing rod 58 and elongated body 14 may include more than one section, and may further include one or more articulating joints.

Handle assembly 12 further includes a locking mechanism 50. Locking mechanism 50 includes a locking member 52 and an engagement member 53 supported on a distal end 52a of locking member 52. The engagement member 53 may comprise an o-ring, or other resilient or frictional member of any shape capable of engaging rotatable member 32. The proximal end 52b of locking member 52 is pivotally mounted to housing 38 about point 50a within barrel portion 30 of handle assembly 12. Distal end 52a of locking member 50 extends from within barrel portion 30 into rotatable member 32. Rotatable member 32 is configured to receive distal end 52a of locking member 52, including o-ring 53. Locking member 52 is configured to be engaged by the distal end 60a of toothed rack 60 during operation of moveable handle 28. A proximal end 52b of locking member 52 includes a cam surface for engagement by distal end 60a of toothed rack 60.

Figure 4:
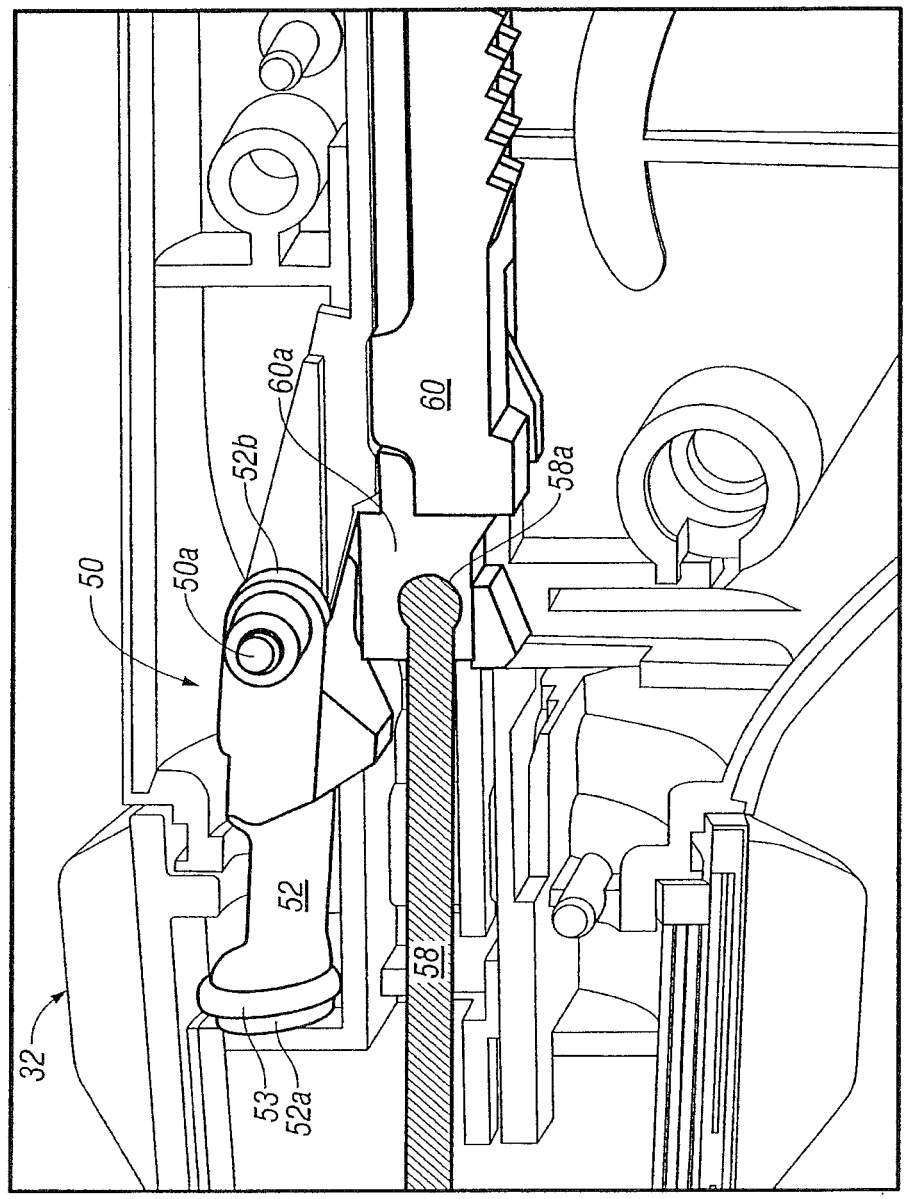
FIG. 4 is a perspective side view of the locking mechanism of the surgical stapling device shown FIGS. 1-3, in an disengaged and unlocked position.
Figure 5:
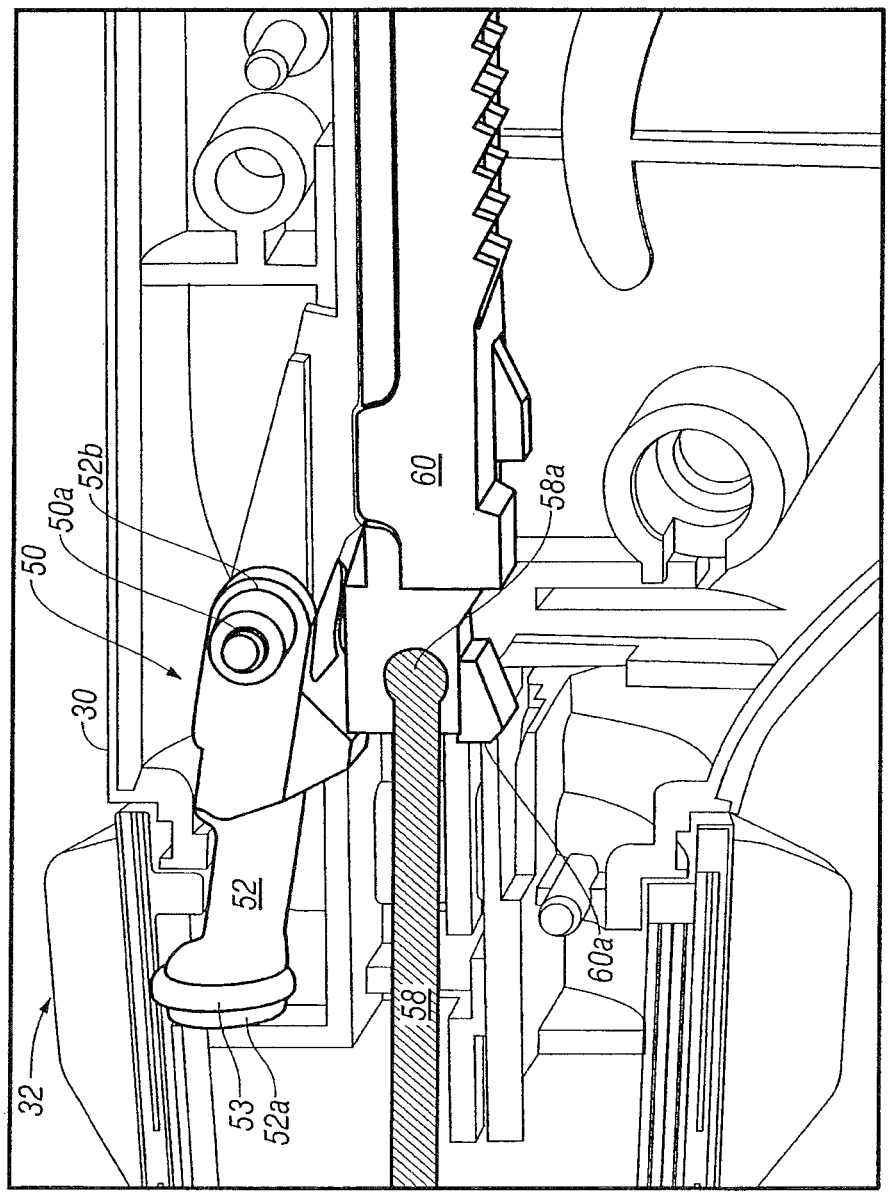
FIG. 5 is a perspective side view of the locking mechanism in FIG. 4, in an engaged and locked position.

Referring now to FIGS. 4 and 5, locking mechanism 50 is maintained in an unlocked position (FIG. 4) prior to actuation of stapling device 10. When locking mechanism 50 is in an unlocked position rotatable member 32 may be freely rotated. In this manner, tool assembly 20 located on distal end 14a of elongated body 14 may be oriented such that cartridge assembly 22 and anvil assembly 24 are in better orientation for grasping the tissue to be stapled.

Upon operation of movable handle 28, actuation mechanism 40 advances toothed rack 60. Advancement of toothed rack 60 causes distal end 60a of toothed rack 60 to engage the cam surface on the proximal end 52b of locking member 52 (FIG. 5). Engagement with toothed rack 60 causes locking member 52 to pivot about point 50a. In this manner, o-ring 53 supported on distal end 52a of locking member 52 is pressed into the inner surface of rotating member 32, frictionally engaging rotatable member 32. In the locked or engaged position, locking mechanism 50 provides resistance to the rotation of rotatable member 32.

Actuation member 40 may be configured such that a release of movable handle 28 causes the retraction of toothed rack 60. For example, toothed rack 60 may be biased in a proximal direction. In an alternate embodiment, toothed rack 60 may be attached to retraction knobs (not show), for retraction of toothed rack 60 manually. The retraction of toothed rack 60 causes distal end 60a of toothed rack 60 to disengage from locking member 52. The disengagement of locking member 52 from toothed rack 60 permits distal end 52a, including o-ring 53, of locking member 52 to pivot away from rotatable member 32. A biasing member, such as a spring, may be used to facilitate such disengagement. In this manner, rotatable member 32 may once again be freely rotated.

During a surgical procedure, stapling device 10 may be used by a surgeon to rotationally manipulate tissue grasped between cartridge assembly 22 and anvil assembly 24. By partially triggering movable handle 28, a surgeon may engage locking mechanism 50 while grasping tissue between cartridge assembly 22 and anvil assembly 24 without discharging the staples. As described above, engagement of locking mechanism 50 provides resistance to the rotation of rotatable member 32. By locking rotatable member 32, the entire stapling device 10 locked in a fixed position and any rotation of handle assembly 12 by the surgeon is directly translated to tool assembly 20. In this manner, the surgeon may use stapling device 10 as surgical forceps to manipulate the tissue grasped between cartridge assembly 22 and anvil assembly 24. Upon release of movable handle 28 the tissue grasped between cartridge assembly 22 and anvil assembly 24 is released and locking mechanism 50 is disengaged. Manipulation of the tissue using stapling device 10 as surgical forceps may be repeated as necessary.

In an alternative embodiment of the present disclosure, the locking member is configured to engage one or more notches defined in the rotatable member so that, as the toothed rack is advanced, the locking member is received in a notch, preventing rotation of the rotatable member.

Figure 6:
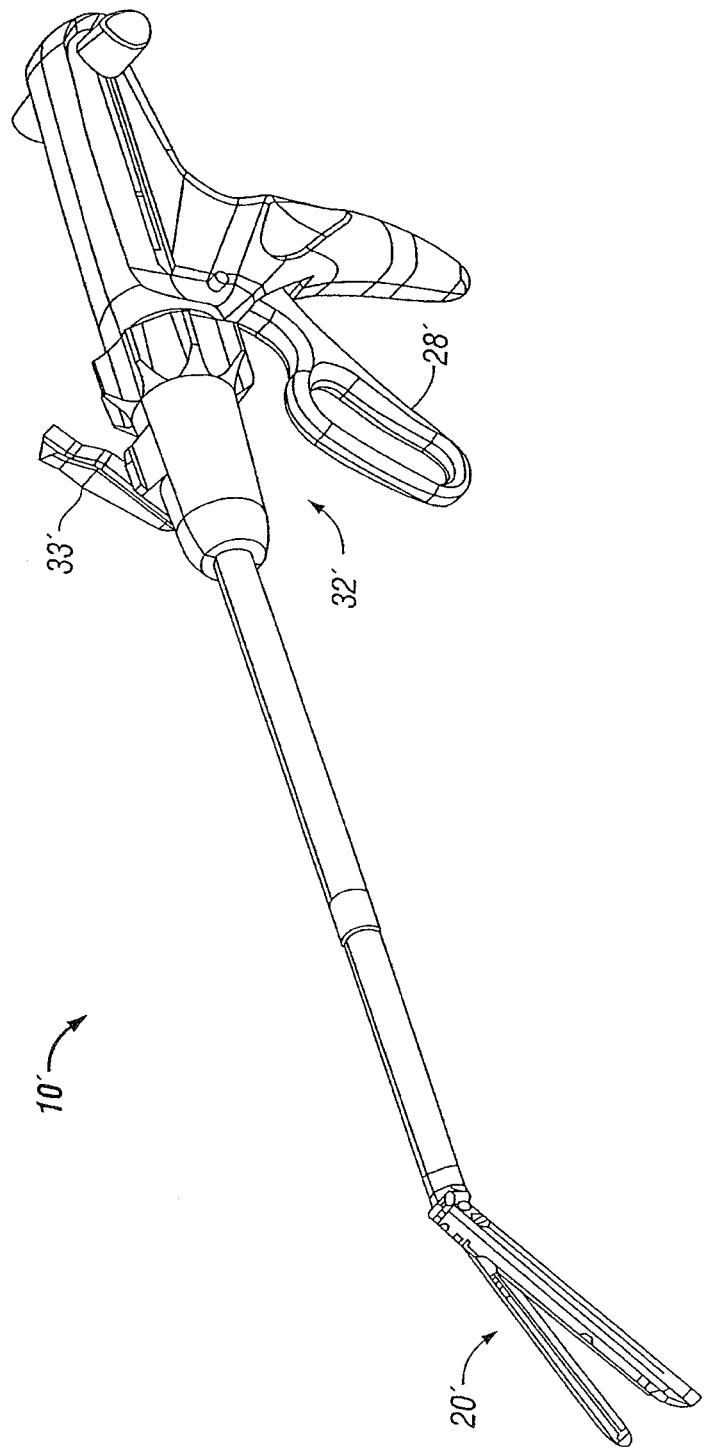
FIG. 6 is a side view of an alternate embodiment of a surgical stapling device having a rotating locking mechanism in accordance with the present disclosure.
Figure 7:
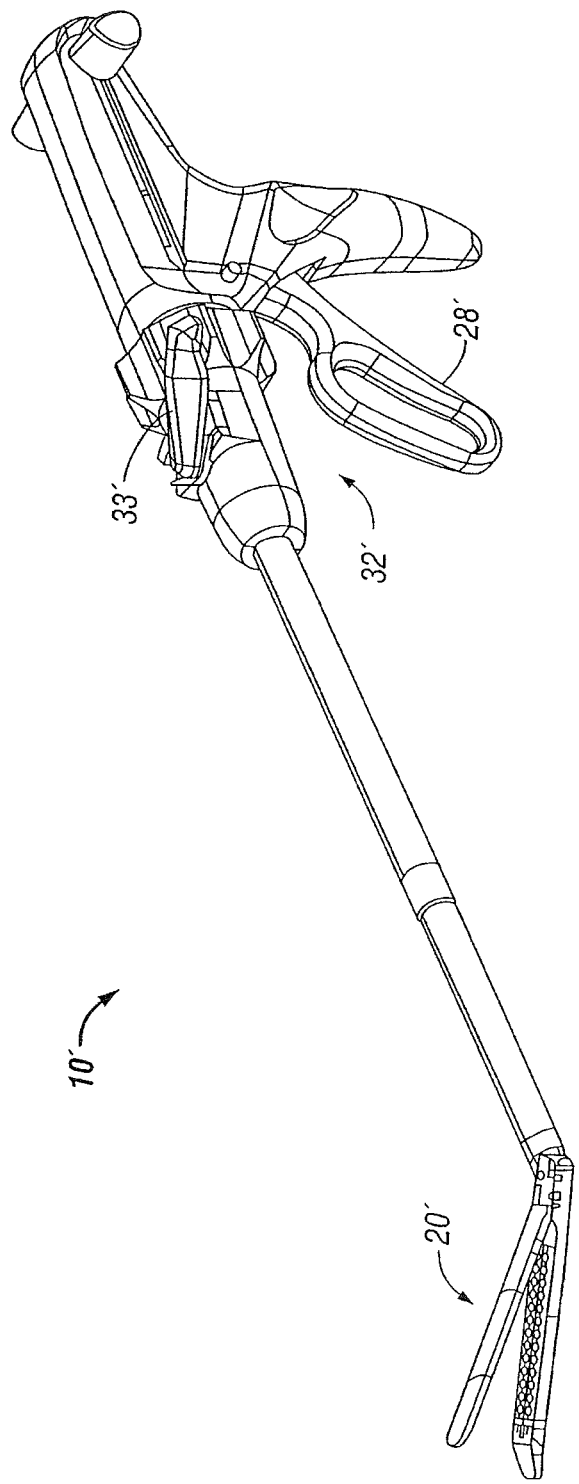
FIG. 7 is a side view of the surgical stapling device of FIG. 6 oriented in a second configuration.
Figure 8:
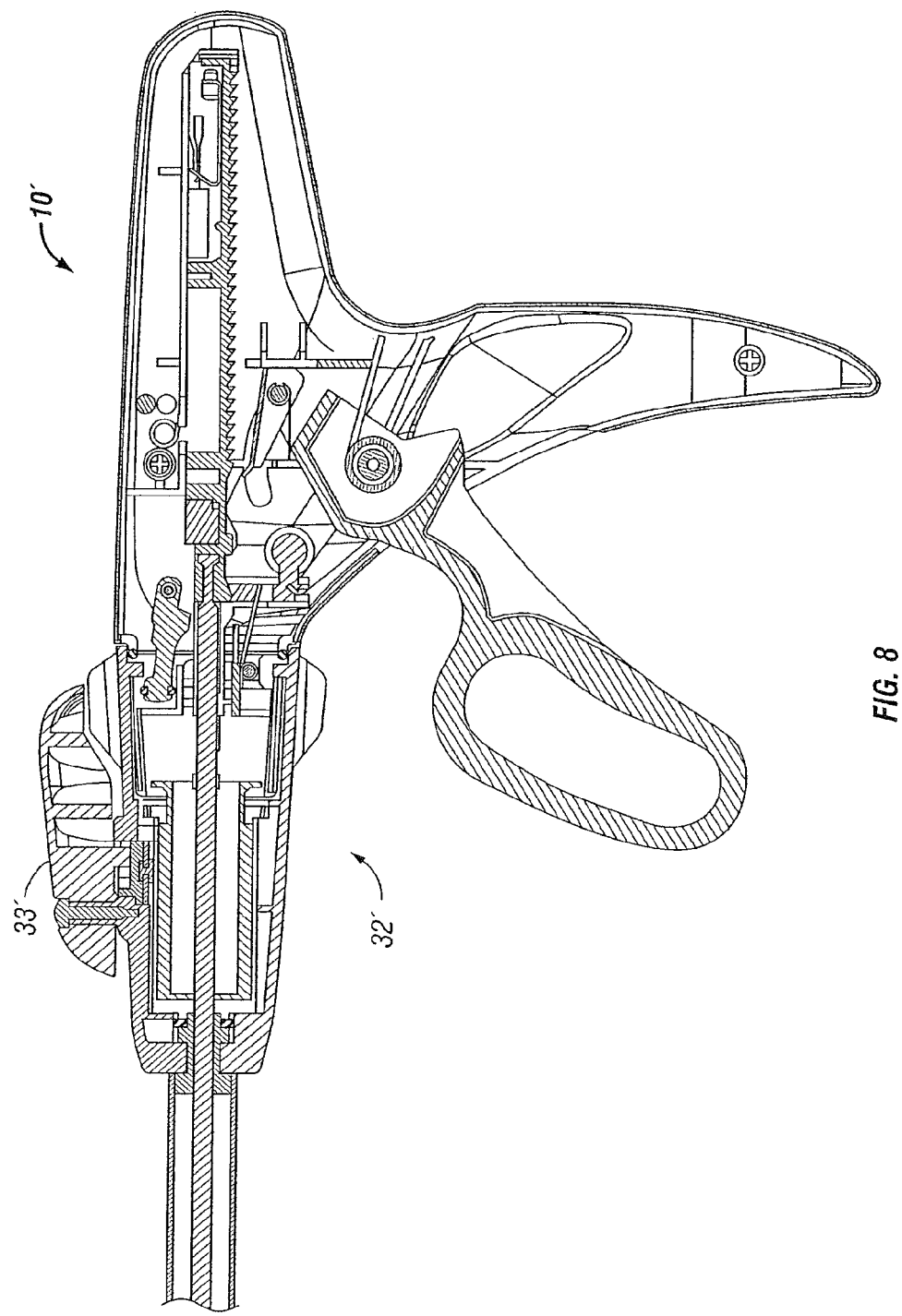
FIG. 8 is a partial cross-sectional side view of the stapling device of FIGS. 6-7.

Referring now to FIGS. 6-8, in an alternate embodiment of the present disclosure a surgical stapling device 10' further includes an articulating tool assembly 20'. Tool assembly 20' is rotated, as described above, using a rotatable member 32'. Articulation of tool assembly 20' is controlled using an articulation member 33' operably disposed on rotatable member 32'.

During a surgical procedure, prior to grasping the tissue to be manipulated and/or stapled, tool assembly 20' of stapling device 10' may be rotated using rotatable member 32' and/or articulated with articulation member 33' to better orient tool assembly 20' for engagement of the tissue. Once tool assembly 20' has been properly oriented, triggering of movable handle 28' results in the engagement of locking mechanism 50' with rotatable member 32' as described above. Locking mechanism 50' (FIG. 8) may be engaged regardless of the rotation or articulation of tool assembly 20'. As described above, locking mechanism 32' provides resistance to, or prevents the rotation of tool assembly 20' while movable handle 28' is triggered. Upon return of movable handle 28' to a released or untriggered position, locking mechanism 32' is unlocked or disengaged, and tool assembly 20' is once again freely rotatable.

It is appreciated that the locking mechanism of the present disclosure may further be incorporated into any number of devices having a rotating shaft, including endoscopic forceps, graspers, hemostats, shears, clamps, etc. It is should also be understood that various changes in form, detail and operation of the rotating knob locking mechanism of the present disclosure may be made without departing from the spirit and scope of the present disclosure. For example, the locking member may include a resilient or frictionally engaging material to provide resistance to the rotation knob against rotating in other embodiments, the locking member comprises a feature for engaging one or a series of notches in the rotation knob to lock the knob in a predetermined position.

What is claimed is:

1. A surgical stapling instrument, comprising:
   a handle assembly having a movable handle;
   a tool assembly having a plurality of surgical staples;
   an elongate shaft defining a longitudinal axis, the elongate shaft mounted with the handle assembly for rotation of the elongate shaft about the longitudinal axis;
   the handle assembly further comprising a firing member extending therefrom and a pivotable locking member mounted in the handle assembly;
   the firing member extending through the elongate shaft and being advanced when the movable handle is moved in a first direction to fire the surgical staples from the tool assembly and;
   the pivotable locking member having a surface for engagement by the firing member when the movable handle is moved in the first direction and a distal end that moves into engagement with the elongate shaft when the surface is engaged by the firing member.

2. The surgical stapling instrument according to claim 1, wherein the distal end of the locking member has an o-ring.

3. The surgical stapling instrument according to claim 1, wherein the elongate shaft includes a rotatable member attached to the elongate shaft so that rotation of the rotatable member rotates the elongate shaft.

4. The surgical stapling instrument according to claim 3, wherein the locking member has a proximal end defining a pivot and the surface of the locking member defines a cam surface.

5. The surgical stapling instrument according to claim 3, wherein the firing member cams the pivotable locking member into engagement with a surface on the elongate shaft.

6. The surgical stapling instrument according to claim 3, wherein the rotatable member defines a notch and the locking member engages the notch when the surface is engaged by the firing member.

7. The surgical stapling instrument according to claim 1, wherein the firing member comprises a toothed rack.

8. The surgical stapling instrument according to claim 7, wherein the movable handle includes a pawl for engaging and disengaging the toothed rack.

9. A surgical stapling instrument, comprising:
   a handle assembly;
   a locking member pivotably mounted within the handle assembly;
   an elongate shaft defining a longitudinal axis, the elongate shaft mounted with the handle assembly for rotation of the elongate shaft about the longitudinal axis;
   a tool assembly located on a distal end of the elongate shaft and including a plurality of surgical staples; and
   a firing member extending through the elongate shaft and being advanced in a first direction to fire the surgical staples from the tool assembly, wherein the locking member includes a surface for engagement by the firing member when the firing member is moved in the first direction and a distal end that moves into engagement with the elongate shaft when the surface is engaged by the firing member.

10. The surgical stapling instrument according to claim 9, wherein the distal end of the locking member includes an o-ring.

11. The surgical stapling instrument according to claim 9, wherein the elongate shaft includes a rotatable member to facilitate rotation of the elongate shaft relative to the handle.

12. The surgical stapling instrument according to claim 11, wherein the firing member pivots the locking member into engagement with a surface on the rotatable member.

13. The surgical stapling instrument according to claim 9, wherein the locking member has a proximal end defining a pivot and the surface of the locking member defines a cam surface.

* * * * *